US011648345B2

United States Patent
Nemoto et al.

(10) Patent No.: US 11,648,345 B2
(45) Date of Patent: May 16, 2023

(54) INJECTION APPARATUS, ACTUATOR, AND A MANUFACTURING METHOD OF INJECTION APPARATUS

(71) Applicant: NEMOTO KYORINDO CO., LTD., Tokyo (JP)

(72) Inventors: Shigeru Nemoto, Tokyo (JP); Takashi Saitoh, Tokyo (JP); Toshio Kanetaka, Tokyo (JP); Takashi Hachiya, Tokyo (JP); Yasufumi Saitoh, Tokyo (JP); Yumiko Fukikoshi, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 158 days.

(21) Appl. No.: 16/484,089

(22) PCT Filed: Feb. 8, 2017

(86) PCT No.: PCT/JP2017/004640
§ 371 (c)(1),
(2) Date: Aug. 6, 2019

(87) PCT Pub. No.: WO2018/146758
PCT Pub. Date: Aug. 16, 2018

(65) Prior Publication Data
US 2020/0001002 A1    Jan. 2, 2020

(51) Int. Cl.
*A61M 5/145* (2006.01)
*A61M 5/168* (2006.01)

(52) U.S. Cl.
CPC ........ *A61M 5/145* (2013.01); *A61M 5/16804* (2013.01); *A61M 2205/33* (2013.01)

(58) Field of Classification Search
CPC .......... A61M 5/16804; A61M 2205/33; A61M 5/14566; A61M 5/1458; A61M 5/14546
See application file for complete search history.

(56) References Cited

U.S. PATENT DOCUMENTS 5,868,710 A * 2/1999 Battiato ............ A61M 5/14546
604/123
6,913,591 B2   7/2005 Itoh et al.
(Continued)

FOREIGN PATENT DOCUMENTS

| EP | 2351590 A2 | 8/2011 |
| JP | H9-122237 A | 5/1997 |
| JP | 2002-272839 A | 9/2002 |

(Continued)

OTHER PUBLICATIONS

The extended European search report issued by the European Patent Office dated Jul. 28, 2020, which corresponds to European Patent Application No. 17896040.7-1122 and is related to U.S. Appl. No. 16/484,089.

(Continued)

*Primary Examiner* — Bradley J Osinski
(74) *Attorney, Agent, or Firm* — Studebaker & Brackett PC (57) ABSTRACT

The injection apparatus 100 is provided that can allow repair or replacement of an actuator 130 while maintaining a drip-proof state, and that can further maintain the drip-proof state without a cover. The injection apparatus 100 includes a syringe holder 110 on which a syringe filled with a liquid medicine is mounted, a presser 115 that pushes out the liquid medicine from the mounted syringe, an actuator 130 that moves the presser 115 forward or backward, the actuator 130 including a feed screw nut 134, a feed screw shaft 133, a motor 132, and a transmission mechanism 180 that transmits rotation from the motor 132 to the feed screw shaft 133, wherein the feed screw nut 134, the feed screw shaft 133, the motor 132, and the transmission mechanism 180 are housed in a case 170 of the actuator 130.

10 Claims, 9 Drawing Sheets

(56) References Cited

U.S. PATENT DOCUMENTS

| | | | |
|---|---|---|---|
| 8,211,057 B2* | 7/2012 | Nemoto | A61M 5/14546 |
| | | | 343/866 |
| 9,545,646 B2 | 1/2017 | Kanetaka et al. | |
| 9,694,146 B2 | 7/2017 | Yamamoto | |
| 2002/0133114 A1 | 9/2002 | Itoh et al. | |
| 2004/0073161 A1* | 4/2004 | Tachibana | A61M 5/1456 |
| | | | 604/67 |
| 2007/0179444 A1* | 8/2007 | Causey | A61M 5/14566 |
| | | | 604/131 |
| 2013/0340608 A1 | 12/2013 | Yamamoto | |
| 2014/0131476 A1* | 5/2014 | Kanetaka | H02N 2/14 |
| | | | 239/102.1 |
| 2015/0157791 A1* | 6/2015 | Desch | G01L 9/0089 |
| | | | 604/506 |

FOREIGN PATENT DOCUMENTS

| | | |
|---|---|---|
| JP | 2013-000207 A | 1/2013 |
| WO | 2012/124028 A1 | 9/2012 |
| WO | 2014/024235 A1 | 2/2014 |

OTHER PUBLICATIONS

Notification of Transmittal of Translation of the International Preliminary Reporton Patentability (Chapter I) and Translation of Written Opinion of the International Searching Authority, PCT/JP2017/004640, dated Aug. 13, 2019.
International Search Report issued in PCT/JP2017/004640; dated May 9, 2017.
Written Opinion issued in PCT/JP2017/004640; dated May 9, 2017.

* cited by examiner

INJECTION APPARATUS, ACTUATOR, AND A MANUFACTURING METHOD OF INJECTION APPARATUS

TECHNICAL FIELD

The present invention relates to an injection apparatus including an actuator, a manufacturing method of the injection apparatus, and the actuator.

BACKGROUND ART

In the technical field related to injection apparatuses of liquid medicines, the configuration is known in which a motor and a drive mechanism including a transmission mechanism, etc. connected to the motor via a shaft are arranged into a frame of an injection head of an injection device. For example, Patent Literature 1 discloses the configuration in which a drive mechanism including a transmission mechanism, a ball screw shaft, and a ball screw nut, and a motor are arranged in a frame. Then, the transmission mechanism includes a pinion gear connected to the motor via a shaft, and a screw gear connected to the ball screw shaft.

CITATION LIST

Patent Literature

PTL 1: Japanese Patent Application Laid-Open No. 2013-000207

SUMMARY OF INVENTION

Technical Problem

In an injection apparatus of a liquid medicine, an actuator including a motor and a drive mechanism is arranged in a cover (frame). Then, drip-proof treatment is performed on the cover so as to prevent the liquid medicine from entering into the actuator. Therefore, in a case where the motor or the drive mechanism is broken down, it has been necessary to open the cover for repair or exchange, and cancel a drip-proof state of the actuator. Therefore, an injection apparatus capable of allowing repair or replacement of the actuator while maintaining the drip-proof state has been required.

Additionally, in a case where a fault occurred in the component parts of the actuator, in the injection device described in Patent Literature 1, it was difficult to disassemble and replace or repair the component parts in the frame. Further, a long time is required to disassemble and replace or repair the component parts in the frame. Therefore, conventionally, it has been necessary to convey the injection apparatus to a factory, etc. for replacement or repair instead of an installation location of the injection apparatus. Therefore, an injection apparatus with which replacement or repair is easily completed at the installation location has been required.

Solution to Problem

In order to solve the above-described problem, an injection apparatus as an example of the present invention includes a syringe holder on which a syringe filled with a liquid medicine is mounted, a presser configured to push out the liquid medicine from the syringe mounted, and an actuator configured to move the presser forward or backward, the actuator including a feed screw nut, a feed screw shaft, a motor, and a transmission mechanism configured to transmit rotation from the motor to the feed screw shaft, wherein the feed screw nut, the feed screw shaft, the motor, and the transmission mechanism are housed in a case of the actuator.

Additionally, an actuator as another example of the present invention includes a feed screw nut, a feed screw shaft, a motor, a transmission mechanism configured to transmit rotation from the motor to the feed screw shaft, and a case housing the feed screw nut, the feed screw shaft, the motor, and the transmission mechanism.

In addition, a manufacturing method of an injection apparatus as another example of the present invention is a manufacturing method of an injection apparatus, the injection apparatus including a syringe holder on which a syringe filled with a liquid medicine is mounted, a presser configured to push out the liquid medicine from the syringe mounted, and an actuator configured to move the presser forward or backward, a case of the actuator including a front block, a first side block, a second side block, a base block, and a rear block, the manufacturing method including, screwing the base block from a rear end surface side of the first side block, screwing the second side block to the first side block, screwing the front block to the first side block and the second side block, screwing the base block from a rear end surface side of the second side block, and screwing the rear block from a rear end surface side of the base block.

Advantageous Effects of Invention

Accordingly, even in a case where a fault occurs in the component parts of the actuator, it is possible to easily replace the actuator at the installation location of the injection apparatus, and to complete repair of the injection apparatus. Additionally, by performing drip-proof treatment on the case of the actuator, even if the cover of the injection apparatus is opened, the drip-proof state is not canceled. Therefore, the repair or replacement of the actuator can be performed while maintaining the drip-proof state. Further, it is possible to provide the injection apparatus that can maintain the drip-proof state without a cover.

Further features of the present invention become clear from the following description of examples that are exemplarily illustrated with reference to the accompanying drawings.

DESCRIPTION OF EMBODIMENTS

Hereinafter, an exemplary embodiment for implementing the present invention is described in detail with reference to the drawings. However, the sizes, materials, shapes and relative positions of components described in the following embodiment are arbitrary, and can be modified according to the configuration or various conditions of an apparatus to which the present invention is applied. Additionally, the scope of the present invention is not limited to the embodiment specifically described below, unless otherwise described. Note that, in this description, up and down correspond to the upper direction and the lower direction in the gravity direction, respectively. Additionally, forward and back correspond to the forward direction in which a presser is separated from an actuator, and the backward direction which is opposite to the forward direction, respectively.

First Embodiment

Figure 1:
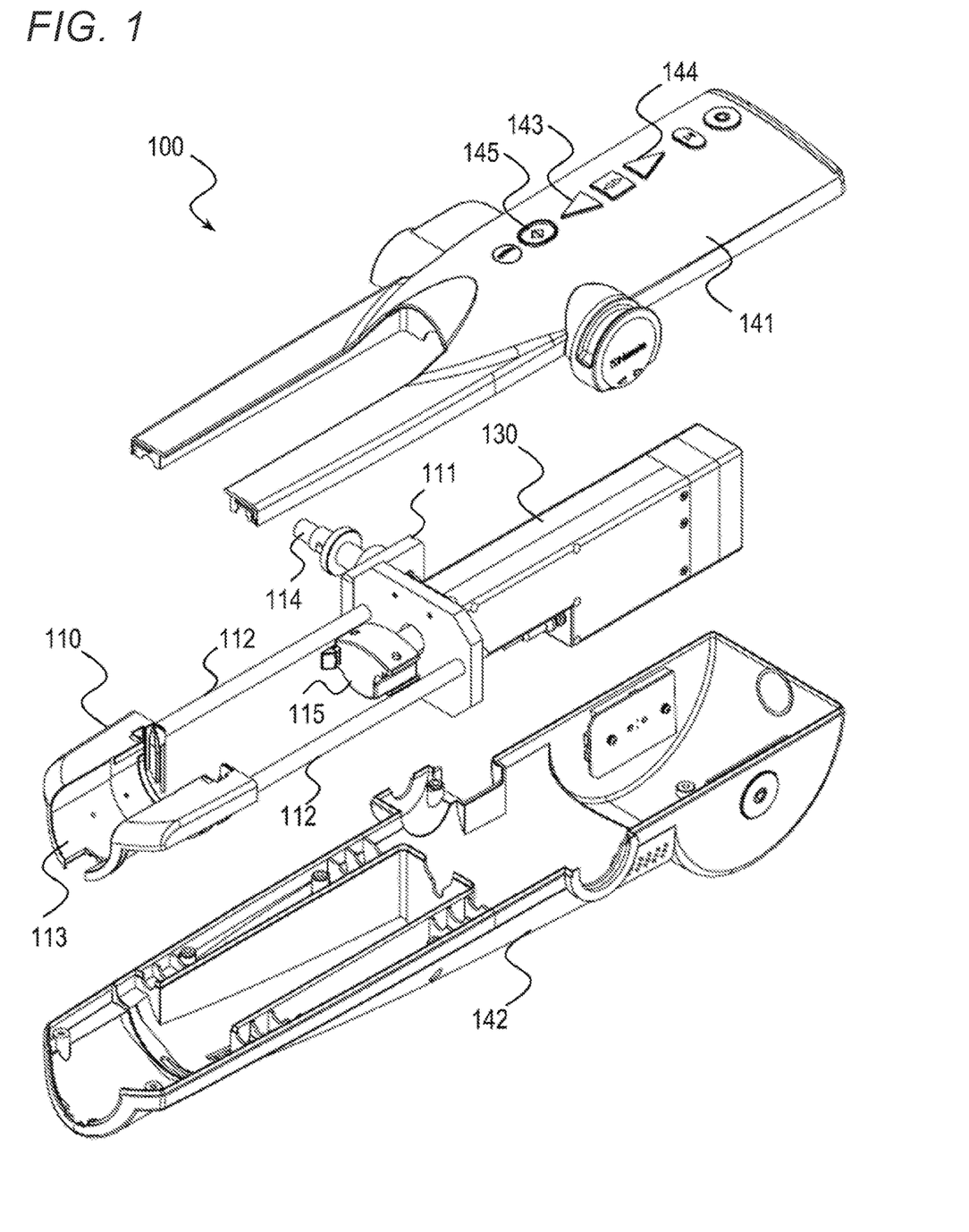
FIG. 1 is a schematic exploded perspective view of an injection apparatus according to a first embodiment.

With reference to FIG. 1, which is a schematic perspective view, an injection apparatus 100 for injecting a liquid medicine is described. The injection apparatus 100 includes, for example, a syringe holder 110 mounting a syringe (not shown) filled with a liquid medicine, such as a contrast agent and a physiological saline solution, a presser 115 that presses a rear end of the mounted syringe (a rear end of a piston), and pushes out the liquid medicine from the mounted syringe, and an actuator 130 that moves the presser 115 forward or backward. Then, the injection apparatus 100 includes an upper cover 141 and a bottom cover 142 that house the actuator 130.

The syringe holder 110 is supported by a pair of supporting portions 112 fixed to the actuator 130 via a substantially L-shaped connecting panel 111. This pair of supporting portions 112 are located on both sides of the presser 115, and extend along the movement direction of the presser 115. Additionally, the syringe holder 110 includes a concave portion 113 for accepting a syringe, and the mounted syringe is fixed to the syringe holder 110. Note that a piston that is slidable in the syringe is attached to the syringe mounted on the injection apparatus 100.

As described later, the actuator 130 includes a feed screw nut, a feed screw shaft, a motor, and a transmission mechanism that transmits rotation from the motor to the feed screw shaft. Then, when the presser 115 is normally rotated in a state where the presser 115 is contacting the rear end of the piston, the presser 115 will press the piston forward. Accordingly, when the piston moves forward, the liquid medicine in the syringe is pushed out, and is injected into a patient's body via an extension tube connected to the tip of the syringe, a mixing device, etc. On the other hand, when the motor is reversed, the presser 115 pulls the piston backward, and the liquid medicine is sucked into the syringe. Note that a nail provided in the presser 115 can be omitted. In a case where the nail is omitted, or in a case where the syringe is removed, when the motor is reversed, only the presser 115 moves backward.

The upper cover 141 is provided with operation buttons, such as a move forward button 143, a move backward button 144, and a start button 145. Additionally, a substrate having a drip-proof structure, which is not shown, is attached to the actuator 130 side of the upper cover 141, and the operation buttons are connected to the substrate. Then, an operator can manually operate the injection apparatus 100 by operating the operation buttons. Specifically, while the operator is pressing the move forward button 143, the presser 115 moves forward. Further, while the operator is pressing the move backward button 144, the presser 115 moves backward. Additionally, when the operator presses the start button 145, the injection apparatus 100 starts injection of a liquid medicine.

The bottom cover 142 is configured so as to engage with the upper cover 141. Then, in a state where the actuator 130 is received, the bottom cover 142 and the upper cover 141 are fixed to each other by a method such as a screw stop. Accordingly, the actuator 130 is housed between the bottom cover 142 and the upper cover 141. Additionally, the injection apparatus 100 includes a connection unit 114 connected to a caster stand (not shown), and the connection unit 114 extends from the connecting panel 111, and is exposed from the bottom cover 142 and the upper cover 141. In addition, the connection unit 114 is being fixed to a front block of the actuator 130 described later.

When the connection unit 114 is connected to the caster stand placed on the floor surface, the injection apparatus 100 is rotatably supported by the caster stand. Accordingly, the injection apparatus 100 can be rotated into a posture in which the front side (the side on which the syringe is mounted) of the injection apparatus 100 is turned to the floor surface, and a posture in which the rear side (the opposite side of the side on which the syringe is mounted) of the injection apparatus 100 is turned to the floor surface. Additionally, it is preferable for the injection apparatus 100 to be connected to the caster stand so as to be able to rotate in a horizontal direction. Note that the connection unit 114 can be connected to a ceiling-hanging member. Then, when the connection unit 114 is connected, the injection apparatus 100 can be hung from a ceiling via the ceiling-hanging member.

Note that the injection apparatus 100 is wiredly or wirelessly connected to a control device that is not shown. This control device includes a touch panel, and functions as a controller of the injection apparatus 100. Additionally, the data of an operation pattern (injection protocol), the data of the liquid medicine, etc. are stored in the control device in advance. Then, in a case where the liquid medicine is injected into a patient, the operator operates the touch panel and inputs an injection speed, an injection amount, an injection time, and the physical data of the patient such as weight, and the liquid medicine data such as the amount of iodine, the kind of the liquid medicine, etc. in the control device.

The control device calculates the optimum injection condition according to the input data and the data stored in advance, and determines the amount of the liquid medicine to be injected into the patient and the injection protocol based on the calculated injection condition. Thereafter, the injection apparatus 100 injects the liquid medicine according to the determined injection protocol. Note that the control device can also obtain the data of the operation pattern (injection protocol) and other data, etc. from an external storage medium.

Figure 2:
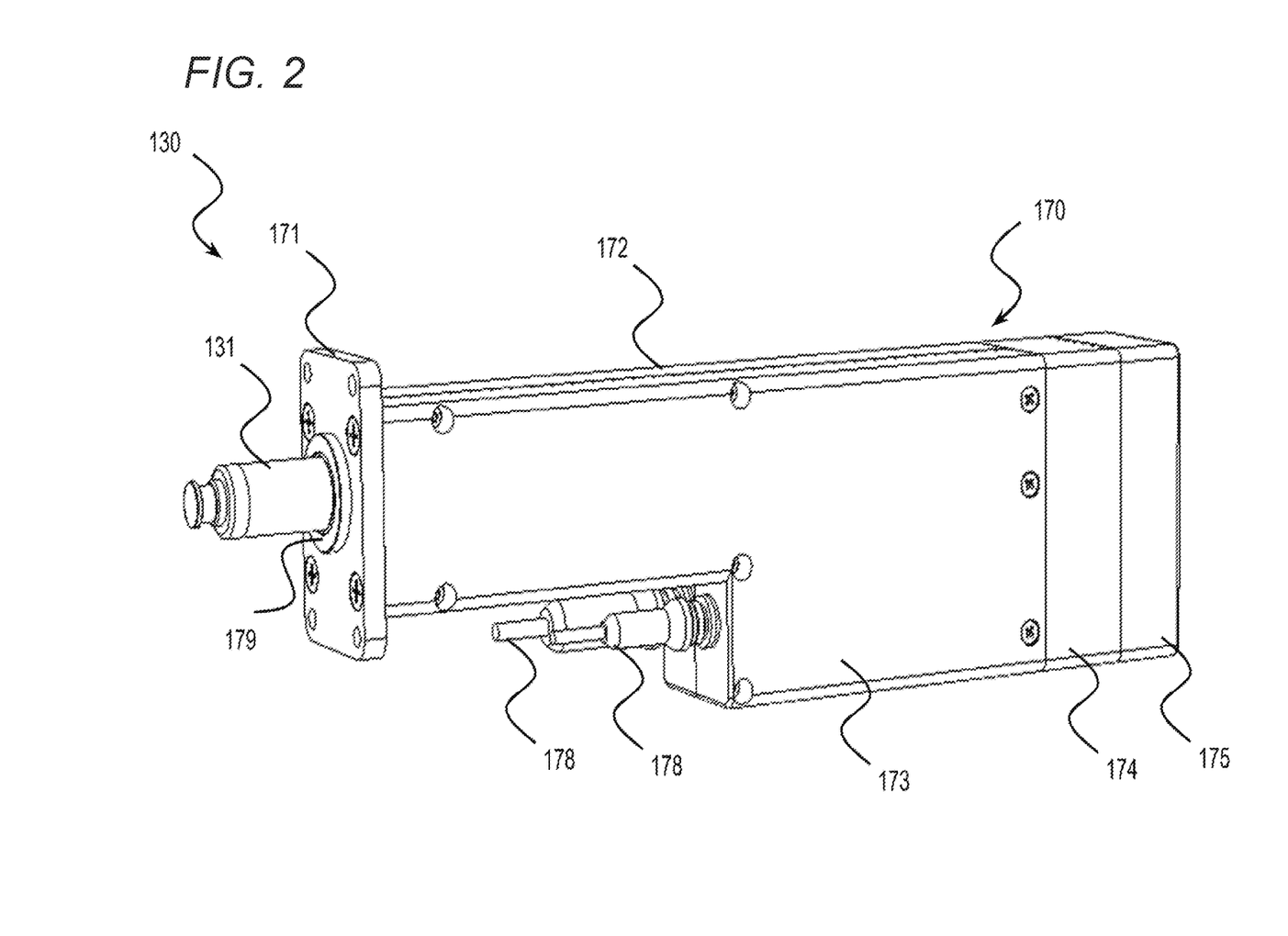
FIG. 2 is a schematic perspective view illustrating the external appearance of an actuator before advancement.
Figure 3:
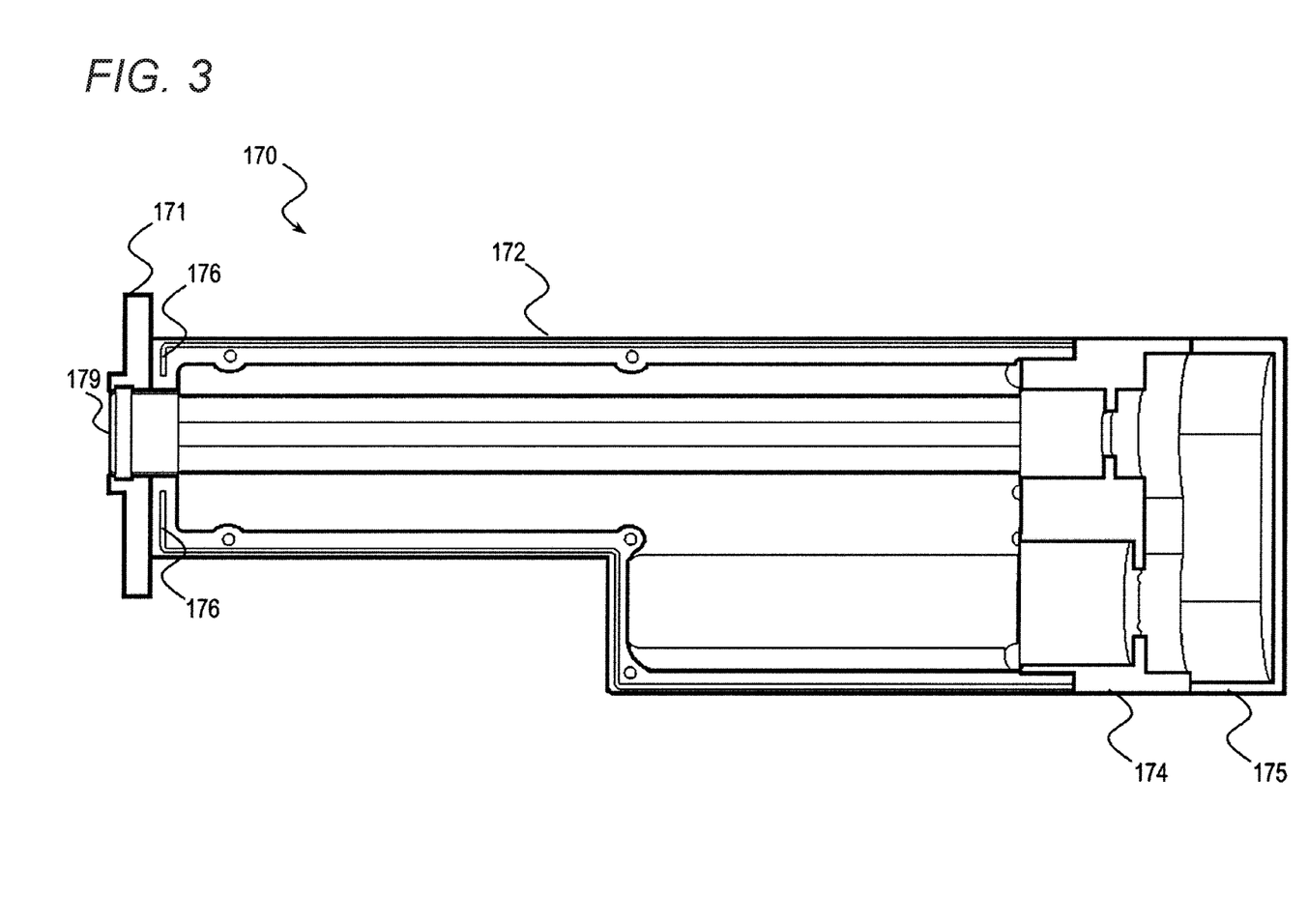
FIG. 3 is a schematic cross-sectional view of a case of the actuator in a longitudinal direction.
Figure 4:
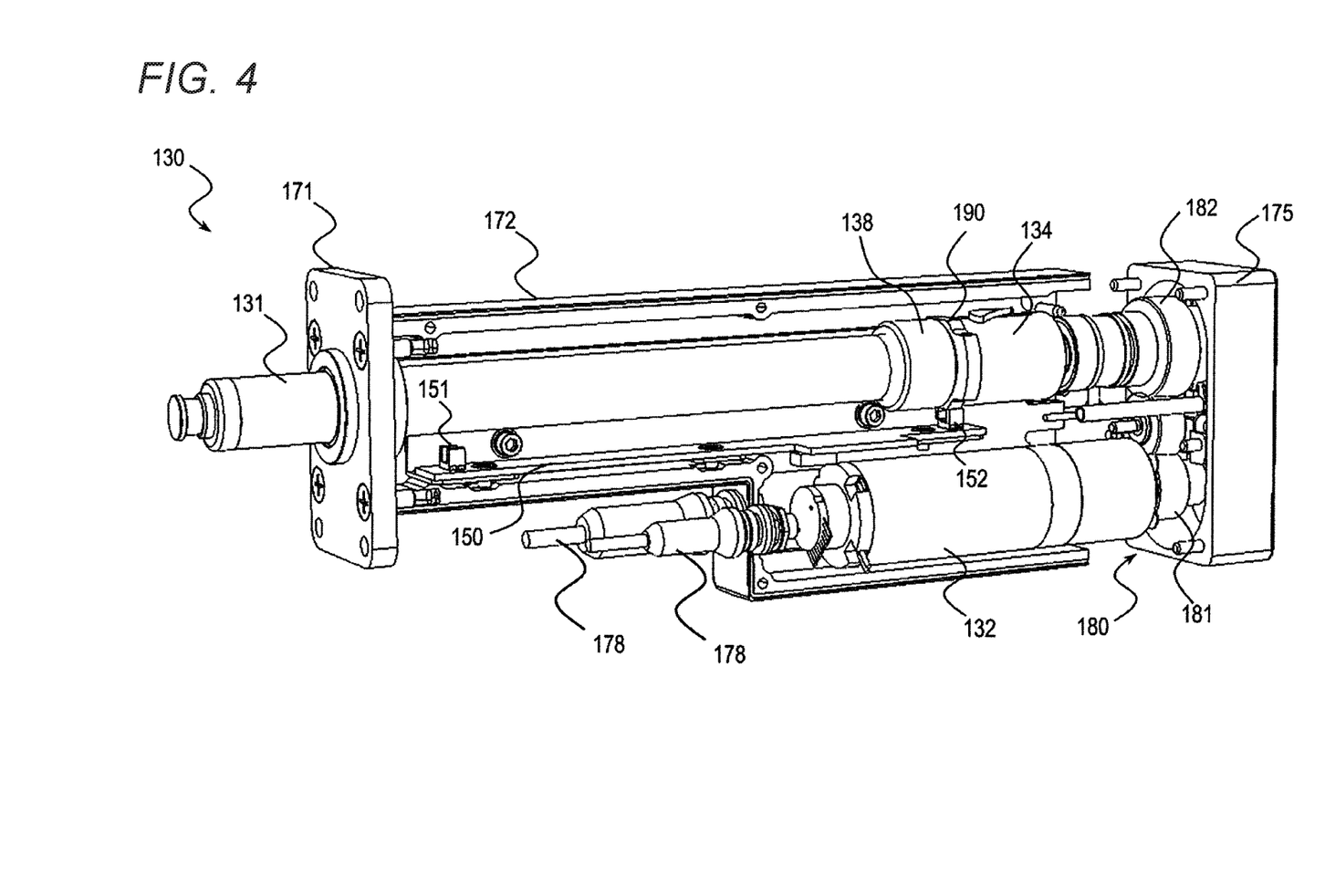
FIG. 4 is a schematic perspective view illustrating the inside of the actuator.
Figure 5:
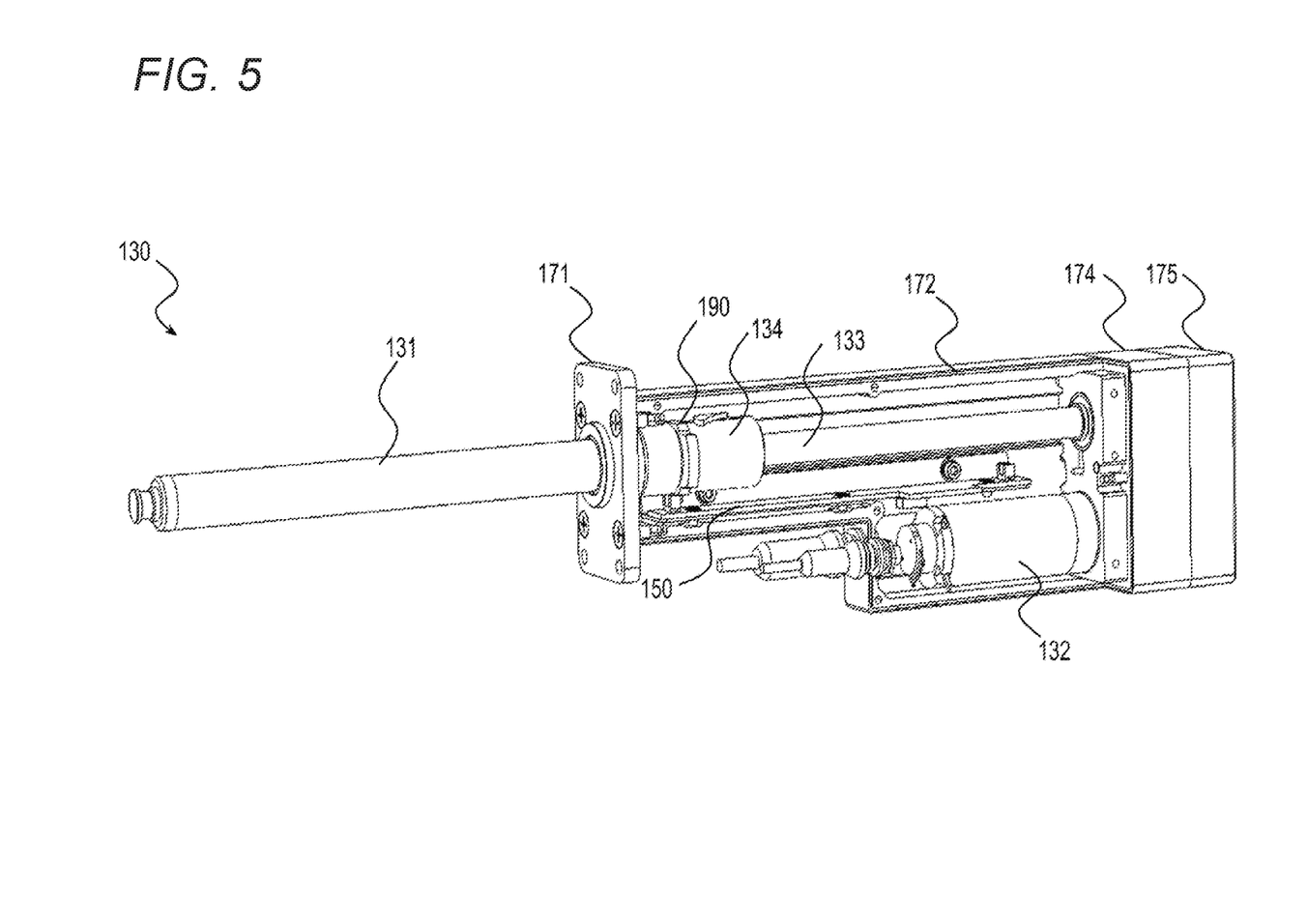
FIG. 5 is a schematic perspective view illustrating the inside of the actuator after advancement.

Subsequently, with reference to FIG. 2 to FIG. 5, the actuator 130 is described. Note that FIG. 2 is a schematic perspective view illustrating the actuator 130 in the state where a pressor pipe 131 is completely moved backward. Additionally, FIG. 3 is a schematic cross-sectional view along the longitudinal direction of a case 170 of the actuator 130. In addition, FIG. 4 is a schematic perspective view for describing the inside of the actuator 130 in the state where the pressor pipe 131 is completely moved backward, and illustration is made by omitting a second side block 173 and a base block 174. Additionally, FIG. 5 is a schematic perspective view for describing the inside of the actuator 130 in the state where the pressor pipe 131 is completely moved forward, and illustration is made by omitting the second side block 173.

As shown in FIG. 2, the actuator 130 includes the case 170 having a front block 171, a first side block 172, the second side block 173, the base block 174, and a rear block 175. In this case 170, the front block 171, the first side block 172 and the second side block 173 fixed to the front block 171 and screwed to each other, the base block 174 fixed to the first side block 172 and the second side block 173, and the rear block 175 fixed to the base block 174 are provided in this order from the front side.

The front block 171 has a plate-like shape, and the connecting panel 111 (FIG. 1) of the syringe holder 110 is fixed to the front block 171. Then, the front block 171 is fixed to front end surfaces of the first side block 172 and the second side block 173.

The first side block 172 and the second side block 173 has substantially L-shaped outer shape. Then, a connector 178, which is electrically connected to the substrate attached to the upper cover 141 extends in the forward direction from the lower parts of the first side block 172 and the second side block 173. Further, the pressor pipe 131 supporting the presser 115 is exposed in the forward direction through a through hole 179 of the front block 171. Note that, in FIG. 2, the pressor pipe 131 is in a completely retracted position.

The base block 174 is being fixed to rear end surfaces of the first side block 172 and the second side block 173 by screwing. Additionally, the inside of the base block 174 is hollow, and the base block 174 has a substantially rectangular outer shape. Then, a screw fixing the base block 174 is inserted in the direction from the base block 174 toward the front block 171. Accordingly, it is possible to support the load applied to the actuator 130 originating from the front block 171 with the screw that extends in the applying direction of the load.

The rear block 175 is fixed to a rear end surface of the base block 174. Additionally, the inside of the rear block 175 is hollow, and the rear block 175 includes a substantially rectangular outer shape. The case 170 including these respective blocks can be formed by die-casting of aluminum. Note that the case 170 can also be formed by resin or carbon fiber.

A seal groove 176 extending along the joining surface of each block is formed in each block of the case 170. For example, as shown in FIG. 3, which is the schematic cross-sectional view of the case 170, the first side block 172 includes the seal groove 176 in the bonding surface with the second side block 173. This seal groove 176 extends while facing the joining surface of the second side block 173. Then, the joining surface of the first side block 172 and the joining surface of the second side block 173 are joined by a liquid sealant applied to the seal groove 176. Accordingly, it is possible to perform drip-proof treatment on the case 170 that houses the actuator 130. Note that the seal groove 176 may be formed in the bonding surface of the second side block 173.

Subsequently, with reference to the internal configuration of the actuator 130 shown in FIG. 4 and FIG. 5, the actuator 130 is described in more detail. Note that, in FIG. 4, the pressor pipe 131 is in a completely retracted position. Additionally, in FIG. 5, the pressor pipe 131 is in a completely advanced position.

The actuator 130 includes a motor 132, a transmission mechanism 180 that transmits the rotation from the motor 132, a ball screw shaft 133 (FIG. 5) as a feed screw shaft connected to the transmission mechanism 180, and a ball screw nut 134 as a feed screw nut attached to the ball screw shaft 133. Then, the case 170 (FIG. 2) houses the ball screw nut 134, the ball screw shaft 133, the motor 132, and the transmission mechanism 180, and accordingly, the actuator 130 is modularized.

As shown in FIG. 4, the actuator 130 includes the pressor pipe 131. Then, the pressor pipe 131 is connected to the ball screw nut 134. This ball screw nut 134 is attached to the ball screw shaft 133. Further, the ball screw shaft 133 is connected to a driven gear 182 of the transmission mechanism 180. Then, the transmission mechanism 180 is connected to a shaft of the motor 132.

A flange member 190 is fit onto a front end of the ball screw nut 134. Then, the flange member 190 is pressed against and fixed to the ball screw nut 134 by fastening a fastening nut 138 attached to a rear end of the pressor pipe 131. This flange member 190 functions as a baffle of the ball screw shaft 133, and prevents aberration of the ball screw nut 134 at the time of moving forward or backward.

Accordingly, the rotation of the shaft of the motor 132 is transmitted to the ball screw shaft 133 via the transmission mechanism 180. Then, the ball screw shaft 133 is rotated according to the transmitted rotation. As a result, the ball screw nut 134 slides in the forward direction or the backward direction with the rotation of the ball screw shaft 133. With this sliding of the ball screw nut 134, the pressor pipe 131 and the presser 115 (FIG. 1) connected to the pressor pipe 131 move forward or backward.

Note that in the state where the actuator 130 is mounted on the injection apparatus 100, the motor 132 is located under the ball screw shaft 133. This motor 132 is a coreless motor (DC coreless motor). Note that, instead of the coreless motor, other motors, such as a stepping motor and an ultrasonic motor, can also be used. However, since the moment of inertia of the coreless motor is small, the coreless motor excels other motors in the responsiveness and the acceleration property.

Additionally, the actuator 130 includes a limit detection unit 150 that detects the limit position of movement of the ball screw nut 134. This limit position is designed to correspond to the position permitted as a limit (design limit) to which the presser 115 can move forward or backward. The limit detection unit 150 extends along the ball screw shaft 133, and includes a front side limit detection unit 151 and a rear side limit detection unit 152. Additionally, the front side limit detection unit 151 and the rear side limit detection unit 152 are provided on a substrate that extends along the ball screw shaft 133. Accordingly, it is possible to detect the limit position of the presser 115 and the pressor pipe 131 that move with the ball screw nut 134. Note that, in FIG. 4, the limit detection unit 150 is arranged on the motor 132 side with respect to the ball screw shaft 133. However, when the limit detection unit 150 is arranged along the ball screw shaft 133, it can also be arranged in other positions.

Figure 6:
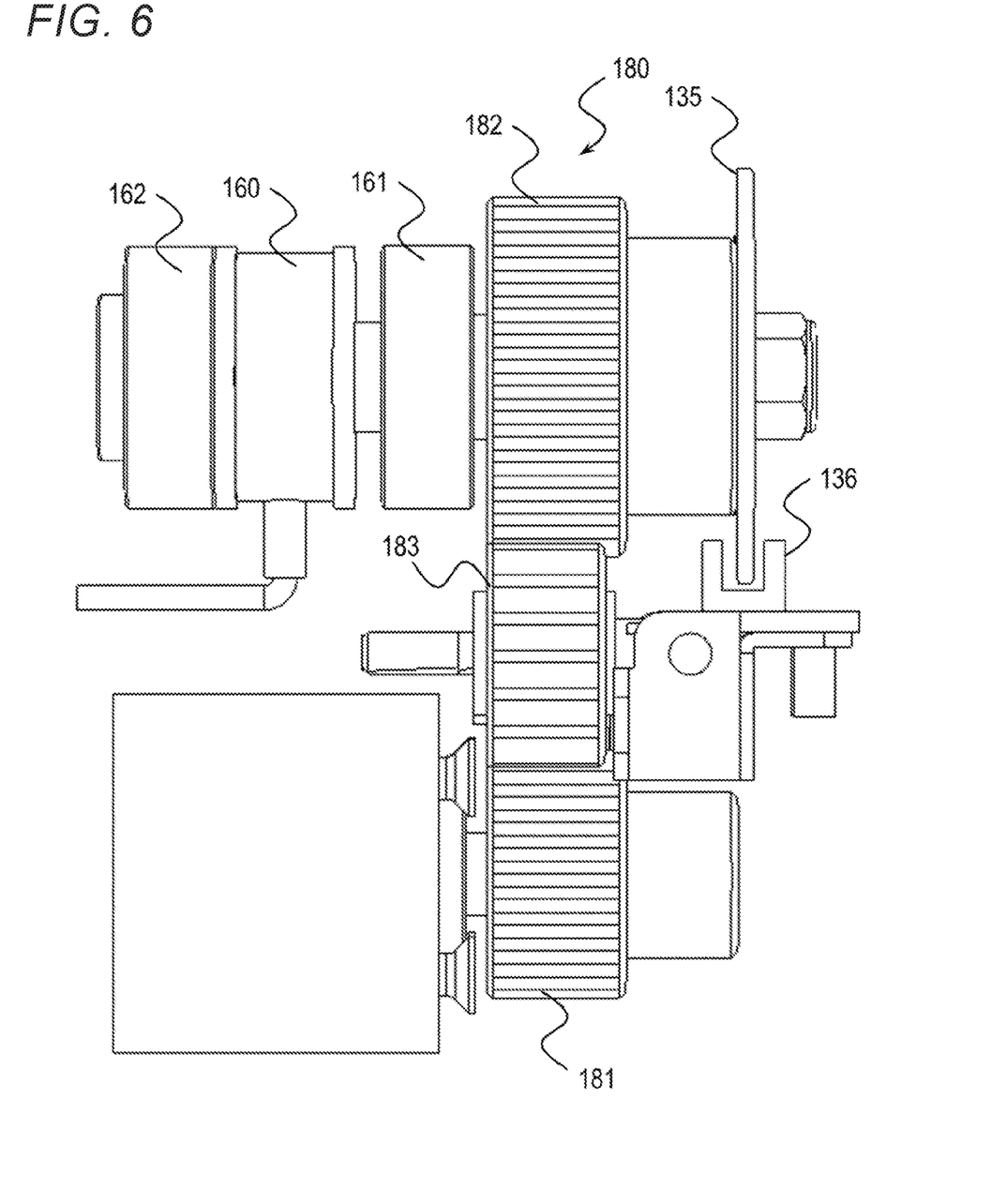
FIG. 6 is a schematic side view of a transmission mechanism.

Subsequently, the transmission mechanism 180 is described with reference to FIG. 6. Note that FIG. 6 shows the transmission mechanism 180 in the state where the transmission mechanism 180 is seen from the side.

The transmission mechanism 180 includes a driving gear 181 connected to the shaft of the motor 132, a driven gear 182 connected to the ball screw shaft 133, and an idle gear 183 located between the driving gear 181 and the driven gear 182. That is, in FIG. 6, the idle gear 183 is located above the driving gear 181, and the driven gear 182 is located above the idle gear 183. Then, the idle gear 183 engages with the driving gear 181 and the driven gear 182. Additionally, behind the driven gear 182, a slit disc 135 and a photo interrupter 136 are arranged. Note that the slit disc 135 and the photo interrupter 136 are housed in the rear block 175 (FIG. 5).

The driving gear 181 and the driven gear 182 are made of a metal, and can be formed of, for example, a steel material, such as stainless steel. Additionally, the idle gear 183 is made of resin, and can be formed of, for example, polyacetal, glass fiber reinforced resin, etc. Note that, although the idle gear 183 may be made of a metal, with the idle gear 183 made of resin, abnormal noise can be prevented. Further, between the transmission mechanism 180 and the ball screw nut 134, a bearing 161, a hollow load cell 160 used for measuring the injection pressure, and an angular ball bearing 162 are sequentially arranged from the rear side.

Figure 7:
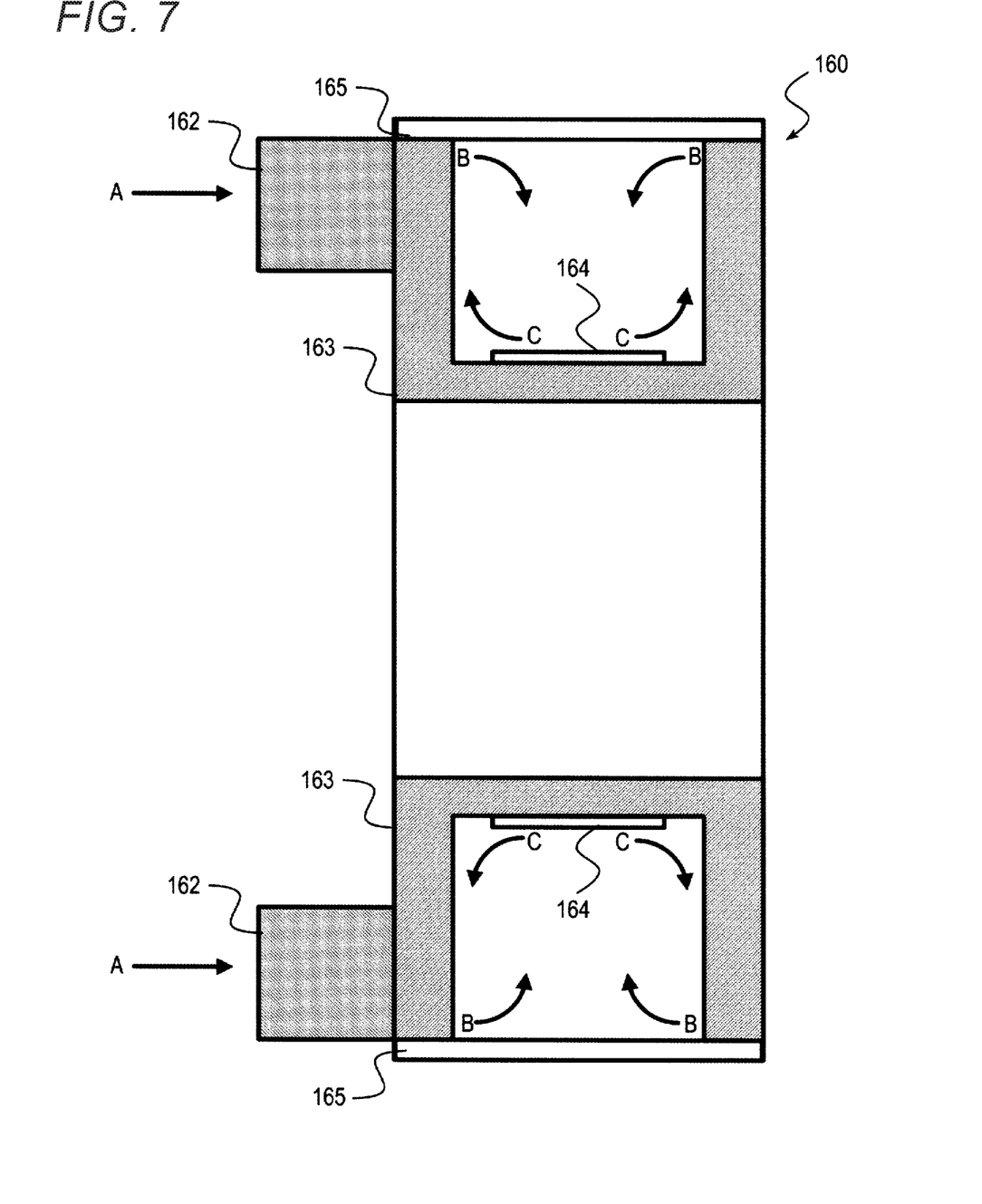
FIG. 7 is a schematic cross-sectional view of a load cell.

This load cell 160 is described in more detail with reference to FIG. 7, which is a schematic cross-sectional view. The load cell 160 includes a substantially bobbin-like hollow member 163, a distortion gage 164 stuck on an outer periphery surface of a body portion of the hollow member 163, and a substantially cylindrical external cylinder 165 that houses the hollow member 163. Note that, although two distortion gages 164 are stuck in the middle of the body portion as an example in FIG. 7, the number of the distortion gage 164 may be three or more, or may be one.

The front end surface of the load cell 160 contacts the angular ball bearing 162. Then, at the time of injection of the liquid medicine, the pressure is applied in the direction indicated by an arrow A. Then, the front end and the rear end of the hollow member 163 are deformed in the direction indicated by an arrow B. As a result, a stretching force in the direction indicated by an arrow C is applied to the body portion of the hollow member 163 and the distortion gage 164. In this manner, since the distortion according to the injection pressure is applied to the distortion gage 164, the injection pressure can be measured by measuring this distortion.

Figure 8:
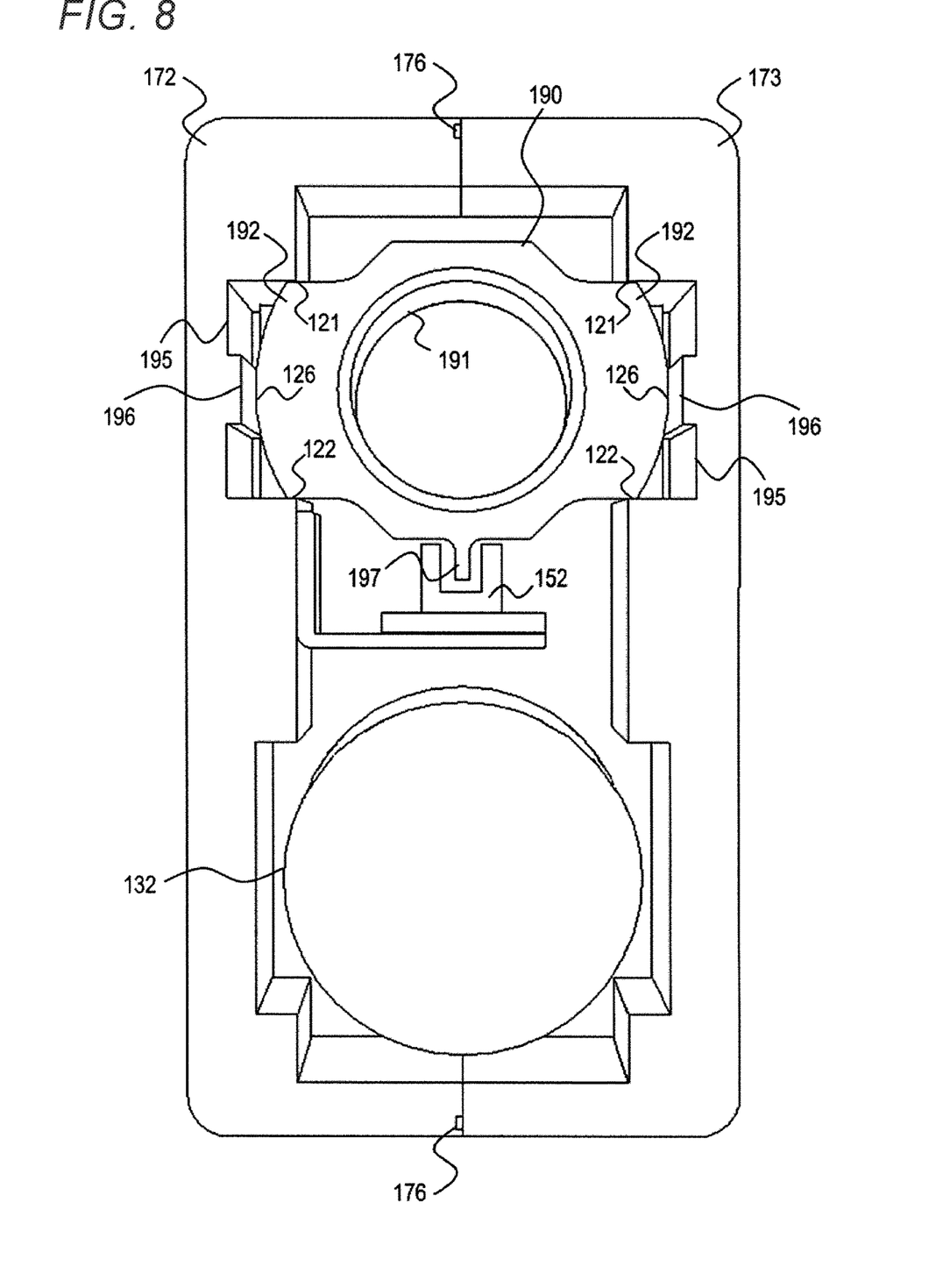
FIG. 8 is a schematic front view of a flange member.

Next, with reference to FIG. 8, the flange member 190 fixed to the ball screw nut 134 is described. Note that FIG. 8 shows the situation of the flange member 190 in the actuator 130 seen from the front side.

A hole 191 in which the front end of the ball screw nut 134 is inserted is formed in the middle of the flange member 190. Then, the flange member 190 is fixed to the ball screw nut 134 by being fastened by the fastening nut 138 (FIG. 4). Additionally, the flange member 190 includes two contact portions 192 on both sides of the hole 191, i.e., the sides facing the first side block 172 and the second side block 173.

On the other hand, the case 170 includes a guide 195 that contacts the contact portion 192 and guides the flange member 190. This guide 195 is formed in each of the first side block 172 and the second side block 173. Then, each of the contact portion 192 includes a first contact surface 121 and a second contact surface 122 that contact the guide 195, and a curving surface 126 provided between the first contact surface 121 and the second contact surface 122.

The second contact surface 122 is located on the motor 132 side of the contact portion 192. Then, the first contact surface 121 is located on the opposite side of the second contact surface 122 across the curving surface 126. In other words, the first contact surface 121 and the second contact surface 122 are external surfaces that extend from both ends of the curving surface 126, respectively, and extend along the longitudinal direction of the ball screw nut 134. Additionally, the curving surface 126 is an external surface that extends in the direction that is perpendicular to the longitudinal direction. Such a flange member 190 can be formed with a low friction resin, for example, iglidur (made from igus, k.k.).

The guide 195 is a groove having a substantially U-shaped cross-section, and extends along the ball screw shaft 133. Then, the first contact surface 121 and the second contact surface 122 contact inner wall surfaces of the guide 195. Additionally, a substantially rectangular protrusion 196 that extends along the ball screw shaft 133 is formed in the middle in the guide 195. Then, the peak of the curving surface 126 contacts the top surface of the protrusion 196. In this manner, since the curving surface 126 and the protrusion 196 make point contact with each other, it is possible to reduce a contact area and to suppress the resistance force applied to the flange member 190. Note that a sliding resin film may be stuck on the flange member 190 or the guide 195, or a lubricant may be applied to the flange member 190 or the guide 195.

In this manner, since the first contact surface 121 and the second contact surface 122 contact the inner wall surfaces of the guide 195, the drag turning of the flange member 190 and the ball screw nut 134 is prevented. Additionally, since the curving surface 126 contacts the protrusion 196, the movement in the direction that is perpendicular to the horizontal direction of the flange member 190 and the ball screw nut 134, i.e., the extending direction of the ball screw shaft 133, is prevented. As a result, it is possible to prevent aberration in advancement or retracting of the ball screw nut 134.

To describe more specifically, in a case where there is no contact surface, the ball screw nut 134 moves in the extending direction of the ball screw shaft 133, i.e., the moving direction of the ball screw nut 134, while shifting slightly so as to draw a spiral trajectory. On this occasion, the directions in which the ball screw nut 134 is shifted are the horizontal direction, and the height direction that is perpendicular to the horizontal direction. Then, the aberration of movement in the height direction is prevented by the first contact surface 121 and the second contact surface 122, and the aberration of movement in the horizontal direction is prevented by the curving surface 126.

Note that the number of the contact portions 192 of the flange member 190 may be only one at one side, or may be three or more. Additionally, the contact portions between the contact portions 192 and the guide 195 may be more than three points. However, the resistance force applied to the flange member 190 can be suppressed by making the number of the contact portions to the minimum.

Additionally, the flange member 190 includes a shield part 197 that shields the limit detection unit 150. This shield part 197 is located in the substantially center of the flange member 190 in the horizontal direction (width direction). In addition, the shield part 197 projects toward the limit detection unit 150, and projects toward the rear side limit detection unit 152 in FIG. 8. Then, the limit detection unit 150 detects the shield part 197.

That is, the shield part 197 moves forward or moves backward with the ball screw nut 134. Then, when the ball screw nut 134 moves backward to the design limit, the shield part 197 shields the rear side limit detection unit 152 of the limit detection unit 150. Further, when the ball screw nut 134 moves forward to the design limit, the shield part 197 shields the front side limit detection unit 151 (FIG. 4) of the limit detection unit 150. Note that, although the shield part 197 is integrally formed with the flange member 190, the shield part 197 formed separately from the flange member 190 may be fixed to the flange member 190.

Figure 9:
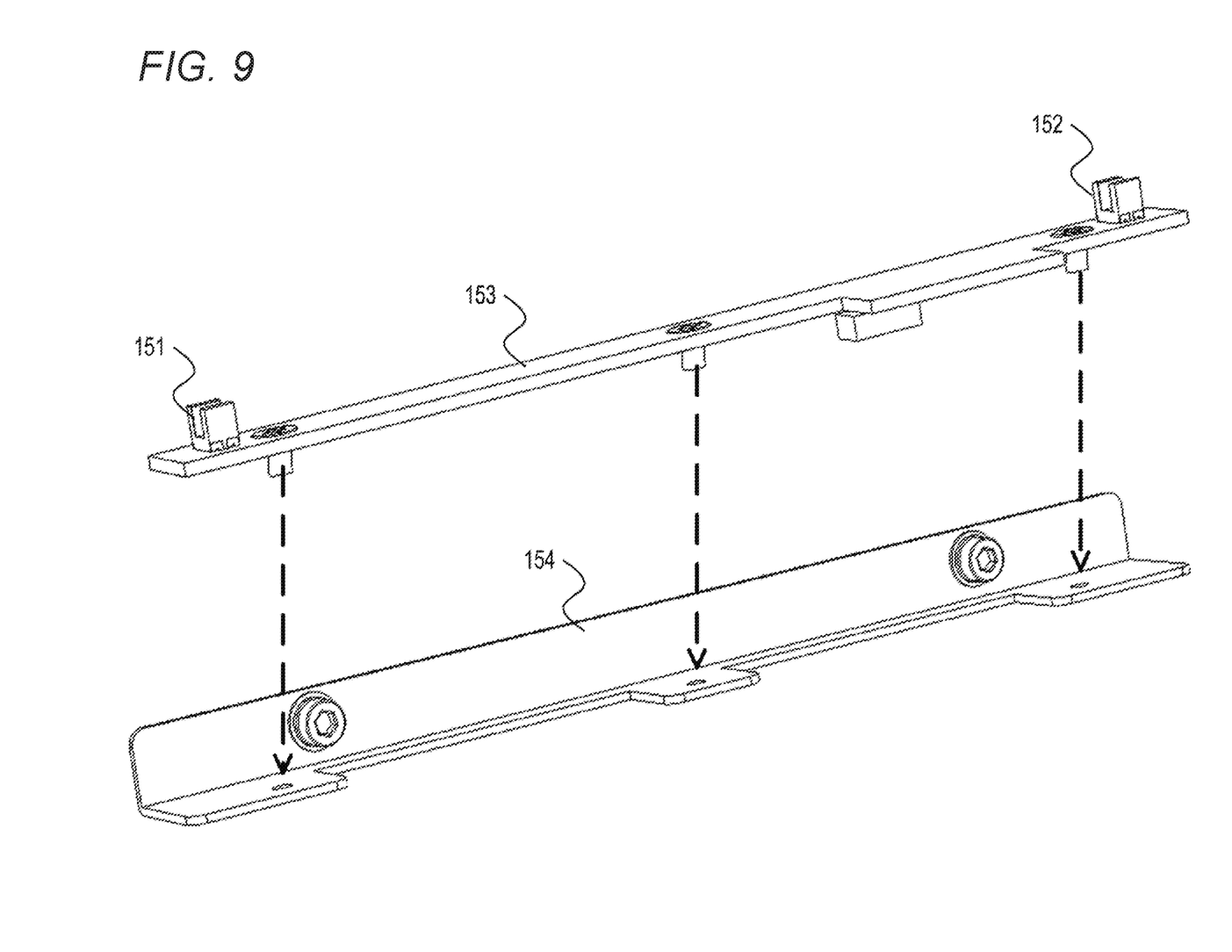
FIG. 9 is a schematic perspective view of a limit detection unit.

With reference to FIG. 9, the limit detection unit 150 is more specifically described. Note that FIG. 9 is a schematic exploded view of the limit detection unit 150.

The front side limit detection unit 151 and the rear side limit detection unit 152 are screwed to an attaching member 154 having an L-shaped cross section via a substrate 153. Then, the attaching member 154 is screwed to an inner wall of the first side block 172. A long hole (not shown) extending along the ball screw shaft 133 is provided in this attaching member 154. Therefore, by moving the attaching member 154 along the long hole, the fixing position of the attaching member 154 with respect to the first side block 172 can be changed to finely adjust the position of the limit detection unit 150. Note that the attaching member 154 may be fixed to an inner wall of the second side block 173.

Additionally, each of the front side limit detection unit 151 and the rear side limit detection unit 152 is an optical slit sensor. Then, the front side limit detection unit 151 detects the design limit for advancement of the presser 115 by detecting the shield part 197. On the other hand, the rear side limit detection unit 152 detects the design limit for retraction of the presser 115 by detecting the shield part 197.

Subsequently, the manufacturing method of the injection apparatus 100 is described. First, in order to manufacture the actuator 130, drip-proof treatment is performed on the first side block 172, the second side block 173, and the base block 174. Specifically, a fluid-sealant is applied to the seal groove 176 of each block. Accordingly, when each of the blocks of the case 170 are screwed to each other in a subsequent process, each of the blocks is fixed in a drip-proof state. Thereafter, the flange member 190 is attached to the ball screw nut 134.

Next, each part is attached to the base block 174. Specifically, the pressor pipe 131, the ball screw nut 134, the angular ball bearing 162, the load cell 160, the bearing 161, the ball screw shaft 133, and the driven gear 182 are attached to the base block 174. Here, when attaching the load cell 160, the load cell 160 is attached so that a preload is applied to the load cell 160. Accordingly, the load cell 160 is attached in a state where the hollow member 163 is slightly deformed. Therefore, in a case where a load is applied to the load cell 160, distortion can be immediately detected. Further, it is possible to prevent a gap from being generated between the load cell 160 and the angular ball bearing 162.

Additionally, when attaching the ball screw shaft 133, the adjustment of the position and posture of the ball screw shaft 133 may be further performed. Note that, when the flange member 190 is fixed to the ball screw nut 134, the fastening nut 138 at the rear end of the pressor pipe 131 is fastened.

Further, an idler shaft and the idle gear 183 are attached to the base block 174. Then, the motor 132 is screwed to the base block 174, and the driving gear 181 is inserted into the shaft of the motor 132. Thereafter, the slit disc 135 and the photo interrupter 136 are attached to the base block 174, and are connected to the connector 178 that is attached to the base block 174 in advance. Note that the attachment of each part to the base block 174 may be performed in any order. Additionally, in a case where the load cell 160 is not required, instead of the load cell 160, a spacer having the same size as the load cell 160 is attached.

Subsequently, the base block 174 is screwed to the first side block 172 from its rear end surface side. On this occasion, the alignment of the flange member 190 and the guide 195 of the first side block 172 is performed. Then, the limit detection unit 150 is attached to the first side block 172 via the attaching member 154. On this occasion, the attaching position of the limit detection unit 150 in the extending direction of the ball screw shaft 133 is adjusted according to the position at which the attaching member 154 is screwed to the first side block 172. Thereafter, a connector of a signal system is connected to a connector of a sensor system.

Next, the second side block 173 is screwed to the first side block 172 so that the respective bonding surface contact each other. Further, the front block 171 is screwed to the first side block 172 and the second side block 173 from both front end surface sides. Here, the position and size of the through hole 179 of the front block 171 are adjusted in advance so as to maintain the straightness of the pressor pipe 131. Therefore, the position and posture of the pressor pipe 131 are automatically adjusted by screwing the front block 171.

Further, the base block 174 is screwed to the second side block 173 from its rear end surface side. Then, the rear block 175 is screwed to the base block 174 from its rear end surface side. Accordingly, an opening of the base block 174 is covered by the rear block 175 so as to receive the slit disc 135 and the photo interrupter 136, etc. In this manner, the actuator 130 can be manufactured. Then, the manufactured actuator 130 is screwed to the connecting panel 111 of the syringe holder 110. Thereafter, the upper cover 141 is put on the syringe holder 110, and the bottom cover 142 is screwed to the upper cover 141 so as to house the actuator 130. In this manner, the injection apparatus 100 can be manufactured.

With the manufacturing method of the actuator 130 according to the above-described first embodiment, since a pulley and a belt do not exist unlike the conventional one, the tension adjustment process of a belt becomes unnecessary. Additionally, since the number of components is less than the conventional one, the number of processes for attaching the components can be reduced. In addition, since the front side limit detection unit 151 and the rear side limit detection unit 152 are integrated, respective positioning becomes unnecessary. Accordingly, the manufacturing time of the actuator 130 can be reduced. Further, with the manufacturing method of the injection apparatus 100 according to the first embodiment, the adjustment of the position and posture of each part at the time of assembling the injection apparatus 100 itself, and the drip-proof treatment can be omitted or simplified by preparing the actuator 130 in advance. Accordingly, the number of manufacturing processes and the manufacturing time of the injection apparatus 100 can be significantly reduced.

Additionally, with the injection apparatus 100 according to the first embodiment, even in a case where a fault occurs in the component parts of the actuator 130, repair can be completed in the installation location of the injection apparatus 100. In addition, by performing the drip-proof treatment on the case 170 in which the actuator 130 is housed, even if the cover of the injection apparatus 100 is opened, the drip-proof state is not canceled. Therefore, repair or replacement of the actuator 130 can be performed while maintaining the drip-proof state, and the drip-proof state can be maintained without the cover. Further, with the case 170 of the actuator 130, it is possible to suppress that the sound generated from the motor 132 and the transmission mechanism 180 leak to the outside. Additionally, with the case 170, it is possible to prevent a lubricating grease applied to the motor 132 and the transmission mechanism 180 from dispersing in the cover of the injection apparatus 100.

Additionally, with the flange member 190 according to the first embodiment, unlike the conventional one, it is not necessary to provide a guide shaft. Therefore, the sizes of the actuator 130 and the injection apparatus 100 can be reduced.

Additionally, with the load cell 160 according to the first embodiment, the load cell 160 is housed in the base block 174 of the actuator 130. Accordingly, the position of the load cell 160 is not changed with respect to the connector 178, and it is not necessary to provide wiring that can move between the load cell 160 and the connector 178. Further, it is not necessary to make the wiring extend to the outer side of the case 170 or the cover on which the drip-proof treatment has been performed. Therefore, it is possible to prevent a liquid from leaking from the gap between the wiring and the case 170 or the cover.

Note that, in first embodiment, the injection apparatus 100 includes one syringe holder 110. However, the injection apparatus 100 may include two or more syringe holders 110. In this case, the injection apparatus 100 includes respective two or more actuators 130 and pressers 115 corresponding to the syringe holders 110.

Additionally, the syringe mounted on the injection apparatus 100 may be any of a syringe filled with a liquid medicine or an empty syringe not filled with a liquid medicine. Then, the syringe filled with the liquid medicine includes a prefilled syringe that is filled with a liquid medicine in advance, a syringe obtained by filling an empty syringe with a liquid medicine by the operator with a suction instrument or a filling instrument, and a syringe obtained by manually filling an empty syringe with a liquid medicine by the operator, etc. Additionally, in a case where an empty syringe not filled with a liquid medicine is mounted on the injection apparatus 100, the operator can fill the syringe with the liquid medicine with an injection apparatus 100, the suction instrument, or the filling instrument. Further, a data carrier, such as a RFID (Radio Frequency Identifier) or a bar code, can be provided in the syringe. The information of the filled liquid medicine, etc. is recorded on this data carrier. Then, the injection apparatus 100 can read the recorded information from the data carrier, and can control the injection pressure of the liquid medicine, etc.

As described above, although the present invention has been described with reference to each embodiment, the present invention is not limited to the above-described embodiment. An invention modified in the scope that does not contradict the present invention, and an invention equivalent to the present invention are also included in the present invention. Additionally, each embodiment and each modification can be properly combined in the scope that does not contradict the present invention.

For example, the injection apparatus 100 can be wiredly or wirelessly connected to an imaging apparatus. Then, at the time of injection of a liquid medicine and photography of an image, various data is transmitted and received between the imaging apparatus and the injection apparatus 100. In this case, for example, the imaging condition may be set or displayed in the injection apparatus 100, or the injection condition may be set or displayed in the imaging apparatus. As such an imaging apparatus, for example, there are various medical imaging apparatus, such as a MRI (Magnetic Resonance Imaging) apparatus, a CT (Computed Tomography) apparatus, an angiography imaging apparatus, a PET (Positron Emission Tomography) apparatus, a SPECT (Single Photon Emission Computed Tomography) apparatus, a CT angiography apparatus, an MR angiography apparatus, an ultrasonic diagnosis apparatus, and a blood vessel imaging apparatus.

Additionally, the injection apparatus 100 can also transmit the information about an injection result (injection history) to and store the information in an external storage apparatus, such as a RIS (Radiology Information System), PACS (Picture Archiving and Communication Systems), and a HIS (Hospital Information System), via a network.

Further, a remote operation apparatus, such as a foot switch and a hand switch, may be wiredly or wirelessly connected to the injection apparatus 100. Instead of the operation buttons, the operator can operate the remote operation apparatus to operate the injection apparatus 100.

Note that, instead of the ball screw shaft 133 and the ball screw nut 134, a trapezoidal thread shaft and a trapezoidal thread nut can be used. However, since a ball is not used, the efficiency of converting the rotational movement into the translatory movement is decreased due to the frictional resistance. Further, due to the frictional resistance, the speed of the presser 115 to move straight is decreased, and the detecting accuracy of the torque applied to the presser 115 is decreased. Therefore, it is more desirable to use the ball screw shaft 133 and the ball screw nut 134.

Additionally, the guide 195 may contact the contact portion 192 of the flange member 190. Therefore, the guide 195 may be a groove having a substantially E-shaped cross-section, and the protrusion 196 may have a semicircular pillar shape. Note that the flange member 190 and the ball screw nut 134 may be fixed by bonding.

Additionally, in a case where the tension adjustment of a belt is not taken into consideration, instead of a gear train including the driving gear 181, the driven gear 182, and the idle gear 183, the transmission mechanism including a driving pulley, a driven pulley, and a timing belt can be used.

Further, in the first embodiment, the actuator 130 is vertically housed between the upper cover 141 and the bottom cover 142, so that the ball screw shaft 133 and the motor 132 are arranged in the up-and-down direction. However, the actuator 130 may be horizontally housed between the upper cover 141 and the bottom cover 142, so that the ball screw shaft 133 and the motor 132 are arranged in the horizontal direction.

REFERENCE SIGNS LIST

100: injection apparatus, 110: syringe holder, 115: presser, 121: first contact surface, 122: second contact surface, 126: curving surface, 130: actuator, 132: motor, 133: feed screw shaft, 134: feed screw nut, 150: limit detection unit, 151: front side limit detection unit, 152: rear side limit detection unit, 170: case, 171: front block, 172: first side block, 173: second side block, 174: base block, 175: rear block, 180: transmission mechanism, 190: flange member, 192: contact portion, 195: guide, 193: contact surface, 197: shield part

The invention claimed is:

1. An injection apparatus comprising:
    a syringe holder on which a syringe filled with a liquid medicine is mounted;
    a presser configured to push out the liquid medicine from the syringe mounted;
    an actuator configured to move the presser forward or backward, the actuator including a feed screw nut including a contact portion, a feed screw shaft, a motor, and a transmission mechanism configured to transmit rotation from the motor to the feed screw shaft;
    a first cover and a second cover configured to engage with each other; and
    a case configured to be housed between the first cover and the second cover, to enclose the feed screw nut and the feed screw shaft on all sides facing the first cover and the second cover, and to include a guide contacting the contact portion and guiding the feed screw nut.

2. The injection apparatus according to claim 1, wherein the case houses the feed screw nut, the feed screw shaft, the motor, and the transmission mechanism.

3. The injection apparatus according to claim 1, wherein a flange member including the contact portion is fixed to the feed screw nut, wherein the contact portion includes a first contact surface and a second contact surface configured to contact the guide, and a curving surface provided between the first contact surface and the second contact surface, and wherein the first contact surface, the second contact surface, and the curving surface face to an inside surface of the case.

4. The injection apparatus according to claim 3, further comprising a limit detection unit configured to detect a limit position of movement of the feed screw nut, wherein the flange member includes a shield part, and the limit detection unit detects the shield part.

5. The injection apparatus according to claim 1, further comprising a limit detection unit configured to detect a limit position of movement of the feed screw nut, wherein the limit detection unit includes a front side limit detection unit and a rear side limit detection unit.

6. The injection apparatus according to claim 1, wherein the motor is a coreless motor.

7. The injection apparatus according to claim 1, wherein the case includes a front block, a first side block, a second side block, a base block, and a rear block, the base block is screwed from a rear end surface side of the first side block;

the second side block is screwed to the first side block;

the front block is screwed to the first side block and the second side block;

the base block is screwed from a rear end surface side of the second side block; and the rear block is screwed from a rear end surface side of the base block.

8. The injection apparatus according to claim 1, wherein the contact portion includes a contact surface configured to make point contact with the guide located on an inside surface of the case so as to decrease the contact resistance between the contact portion and the guide.

9. The injection apparatus according to claim 1, wherein the case includes first and second side portions that engage with each other with a seam at top and bottom sides of the injection apparatus, and the first cover and the second cover engage with each other with a seam at left and right sides of the injection apparatus.

10. An injection apparatus comprising:

a syringe holder on which a syringe filled with a liquid medicine is mounted;

a presser configured to push out the liquid medicine from the syringe mounted;

an actuator configured to move the presser forward or backward, the actuator including a feed screw nut including a contact portion, a feed screw shaft, a motor, and a transmission mechanism configured to transmit rotation from the motor to the feed screw shaft;

a first cover and a second cover configured to engage with each other; and a case configured to be housed between the first cover and the second cover, to house the feed screw nut and the feed screw shaft, and to include a guide contacting the contact portion and guiding the feed screw nut, wherein the contact portion includes a contact surface configured to make point contact with the guide, and wherein the contact surface includes a curving surface, and the contact portion makes a point contact with the guide at the top of the curving surface.

* * * * *